United States Patent [19]

Robert et al.

[11] Patent Number: 5,712,294

[45] Date of Patent: Jan. 27, 1998

[54] N-PYRIDYL CARBOXAMIDES AND DERIVATIVES

[75] Inventors: Jean-Michel Robert; Odile Rideau; Sylvie Robert-Piessard; Jacqueline Courant, all of Nantes; Guillaume Le Baut, Saint Sebatien Sur Loire; Daniel-Henri Caignard, Paris; Pierre Renard, Versailles; Gérard Adam, Le Mesnil Le Roi, all of France

[73] Assignee: Adir Et Compagnie, Courbevoie, France

[21] Appl. No.: 450,346

[22] Filed: May 25, 1995

[30] Foreign Application Priority Data

May 27, 1994 [FR] France ................... 94 06412

[51] Int. Cl.[6] ............ C07D 409/12; C07D 401/12; A61K 31/44
[52] U.S. Cl. ............ 514/336; 514/337; 546/281.4; 546/281.1; 546/283.1; 546/279.1; 546/262; 546/193; 546/282.7; 546/272.1; 546/277.1; 546/265; 544/405
[58] Field of Search ............ 514/336, 337; 546/281.4, 281.1

[56] References Cited

U.S. PATENT DOCUMENTS 2,876,235  3/1959  Voegtli ................... 260/330.5
5,260,320  11/1993  Haga et al. ............... 514/336

FOREIGN PATENT DOCUMENTS 465913  6/1991  European Pat. Off. .

OTHER PUBLICATIONS

El-Kerdawy, M.M. et al. *Chemical Abstract* 84:150558, searched by STN (1976).

*Primary Examiner*—Mukund J. Shah
*Assistant Examiner*—King Lit Wong
*Attorney, Agent, or Firm*—The Firm of Gordon W. Hueschen

[57] ABSTRACT

A compound selected from those of formula (I):

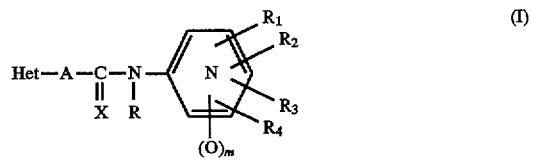

where m is equal to 0 or 1 and

Het, A, X, R, $R_1$, $R_2$, $R_3$, $R_4$ and the ring

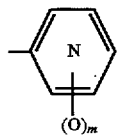

are defined in the description, and a medicinal product comprising the same for treating an inflammatory disorder.

12 Claims, No Drawings

N-PYRIDYL CARBOXAMIDES AND DERIVATIVES

The present invention relates to novel N-pyridyl carboxamides and derivatives, to processes for their preparation and to the pharmaceutical compositions which contain them.

N-Pyridyl carboxamide structures are already described. Thus, patent application WO 9304580 describes N-(4-pyridyl)arylacetamides as pesticides.

The Applicant has now discovered that novel N-pyridyl carboxamide derivatives were non-toxic derivatives endowed with high-level anti-inflammatory and/or diuretic properties. The anti-inflammatory activity of the derivatives of the invention has the particularly advantageous feature of manifesting itself after systemic administration, but also after topical administration, which, besides the standard indications of anti-inflammatory agents, renders the compounds of the invention particularly valuable in skin diseases such as psoriasis. In addition, the diuretic component of certain products of the invention makes them very valuable in certain renal inflammatory diseases.

The invention more specifically relates to the derivatives of formula (I):

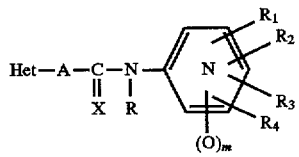

in which
m is equal to 0 or 1,
the symbol

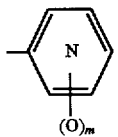

representing the pyridine ring when m is equal to 0 and pyridine N-oxide when m is equal to 1,
the pyridine system

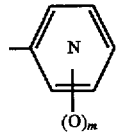

being to the group

which bears it either in the 2-position or in the 3-position of pyridine;

$R_1$ and $R_2$, which may be identical or different, are chosen, independently of each other, from hydrogen, amino, alkylamino, dialkylamino, alkyl, hydroxy, alkoxy, nitro and halogen, $R_3$ and $R_4$, which may be identical or different, are chosen, independently of each other, from amino, alkylamino, dialkylamino, alkyl, hydroxy, alkoxy, nitro and halogen, R represents a hydrogen atom or an alkyl group, A represents a single bond; and in this case Het represents a group chosen from pyrazine, substituted pyrazine, benzothiophene, substituted benzothiophene, 4-oxo[4H]benzopyran, substituted 4-oxo[4H]benzopyran, pyrrole, substituted pyrrole, pyrroline, substituted pyrroline, pyrrolidine, substituted pyrrolidine, piperidine, substituted piperidine, pyridine, substituted pyridine, benzopyran, benzopyran substituted with one or more alkyl groups, chromane, chromane substituted with one or more alkyl groups, 3-carboxy-5-alkylisoxazole, 3-alkoxycarbonyl-5-alkylisoxazole, phthalimido and substituted phthalimido, or alternatively A represents an alkylene group which is unsubstituted or substituted with one or more alkyl groups, or an alkenylene group which is unsubstituted or substituted with one or more alkyl groups; and in this case Het represents a group chosen from thiophene, substituted thiophene, pyrazine, substituted pyrazine, benzothiophene, substituted benzothiophene, 4-oxo[4H]benzopyran, substituted 4-oxo[4H]benzopyran, pyrrole, substituted pyrrole, pyrroline, substituted pyrroline, pyrrolidine, substituted pyrrolidine, piperidine, substituted piperidine, pyridine, substituted pyridine, benzopyran, benzopyran substituted with one or more alkyl groups, chromane, chromane substituted with one or more alkyl groups, 3-carboxy-5-alkylisoxazole, 3-alkoxycarbonyl-5-alkylisoxazole, phthalimido and substituted phthalimido, X represents an oxygen atom, a sulfur atom, an imino group or an imino group substituted with a group chosen from alkyl, alkoxy, hydroxy, amino, arylalkyloxy and aryloxy, the enantiomers and diastereoisomers thereof and the addition salts thereof with a pharmaceutically acceptable acid or base, it being understood that, except where otherwise mentioned:
the term "substituted" relating to the thiophene, pyrazine, benzothiophene, 4-oxo-[4H]benzopyran, pyrrole, pyrroline, pyrrolidine, piperidine, pyridine and phthalimido systems means that these systems are substituted with one or more groups chosen from alkyl, alkoxy, trifluoromethyl, hydroxy, halogen, thiol and alkylthio, the terms "alkyl", "alkoxy" and "alkylene", denote linear or branched groups containing from 1 to 6 carbon atoms, the term "aryl" denotes a phenyl or naphthyl radical,
the term "alkenylene" denotes a linear or branched unsaturated chain containing from 2 to 6 carbon atoms.

Among the pharmaceutically acceptable acids which may be added to the compounds of formula (I) in order to form a salt, there may be mentioned, without any limitation, hydrochloric acid, sulfuric acid, tartaric acid, maleic acid, fumaric acid, oxalic acid, methanesulfonic acid and camphoric acid.

Among the pharmaceutically acceptable bases which may be used in order to salify the compounds of the invention, non-exhaustive examples which may be mentioned are sodium hydroxide, potassium hydroxide, triethylamine, diethylamine, ethanolamine or diethanolamine, arginine and lysine.

The invention relates particularly to the compounds of formula (I) in which, taken together or separately, the symbol

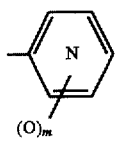

represents a 2-pyridyl group,
the symbol

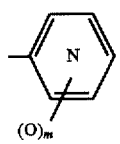

represents a 3-pyridyl group, two of the substituents $R_1$, $R_2$, $R_3$ and $R_4$ represent a methyl radical, R represents a hydrogen X represents a sulfur, X represents an imino group, X represents an imino group substituted with a hydroxyl group, a methoxy group, a methyl group or an amino group, A represents a methylene, Het represents a thiophene or substituted thiophene group,
Het represents a pyrazine or substituted pyrazine group,
Het represents a benzothiophene or substituted benzothiophene group,
Het represents a 4-oxo[4H]benzopyran or substituted 4-oxo[4H]benzopyran group,
Het represents a pyrrole or substituted pyrrole group,
Het represents a pyrrolidine or substituted pyrrolidine group,
Het represents a pyridine or substituted pyridine group,
Het represents a phthalimido or substituted phthalimido group,
Het represents a 3-carboxy-5-methylisoxazole group,
and Het represents a 3-ethoxycarbonyl-5-methylisoxazole group.

Particular cases of the invention relate, for example, to:
the compounds having the formula (IA):

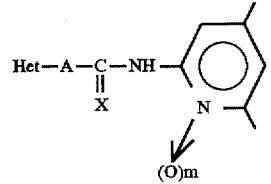

in which
m represents 0 or 1, and
either Het represents the thiophene group and A represents a methylene,
or Het represents the pyrazine group or the pyrazine group substituted with an alkyl group and A is a single bond, and
X represents an oxygen atom, a sulfur atom, an imino group or an imino group substitued with a hydroxyl group, a methoxy group, a methyl group, an amino group or a benzyloxy group, the enantiomers and diastereoisomers thereof and the addition salts thereof with a pharmaceutically acceptable acid, the compound which is N-(4,6-dimethyl-2-pyridyl)-2-thienylacetamide, the N-oxide thereof and the addition salts thereof with a pharmaceutically acceptable acid, the compound which is N-(4,6-dimethyl-2-pyridyl)-3-thienylacetamide, the N-oxide thereof and the addition salts thereof with a pharmaceutically acceptable acid, the compound which is N-(4,6-dimethyl-2-pyridyl)-2-pyrazinylcarbamidoxime of formula

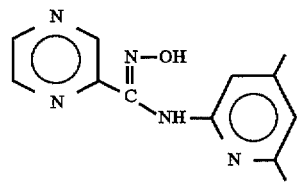

the N-oxide thereof and the addition salts thereof with a pharmaceutically acceptable acid, the compound which is N-(4,6-dimethyl-2-pyridyl)-O-methyl(2-pyrazinyl)carbamidoxime of formula

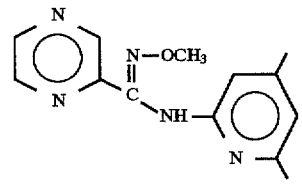

the N-oxide thereof and the addition salts thereof with a pharmaceutically acceptable acid, the compound which is N-(4,6-dimethyl-2-pyridyl)(5-methyl-2-pyrazinyl)thiocarboxamide, the N-oxide thereof and the addition salts thereof with a pharmaceutically acceptable acid, the compound which is N-(4,6-dimethyl-2-pyridyl)(2-pyrazinyl)carboxamidine, the N-oxide thereof and the addition salts thereof with a pharmaceutically acceptable acid, the compound which is N-(4,6-dimethyl-2-pyridyl)-N'-methyl-2-pyrazinylcarboxamidine

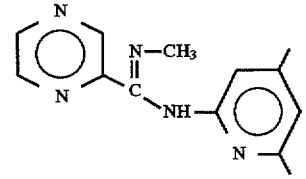

the N-oxide thereof and the addition salts thereof with a pharmaceutically acceptable acid.

The subject of the present invention is also the process for the preparation of the compounds of formula (I), wherein a compound of formula (1):

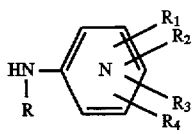 (1)

where

R, $R_1$, $R_2$, $R_3$, $R_4$ and the ring

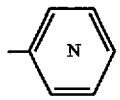

have the same definition as in formula (I), is used as starting material
which derivative is either condensed with a derivative of formula (2):

Het—A—COOH (2)

where

Het and A have the same definition as in the formula (I), to give a derivative of formula (I/a):

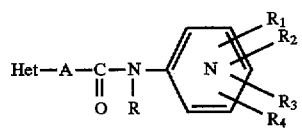 (I/a)

where

Het, A, R, $R_1$, $R_2$, $R_3$, et $R_4$ and the ring

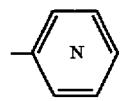

have the same definition as above,
which derivative of formula (I/a) is subjected to a thionating agent to give a derivative of formula (I/b):

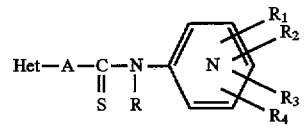 (I/b)

where

Het, A, R, $R_1$, $R_2$, $R_3$ et $R_4$ and the ring

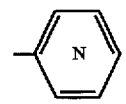

have the same meaning as above,
which derivative of formula (I/b) is condensed with a derivative of formula (3):

NH—Z (3)

where

Z represents a hydrogen atom or a hydroxyl, alkyl, alkoxy, amino, arylalkyloxy or aryloxy group, to give a derivative of formula (I/c):

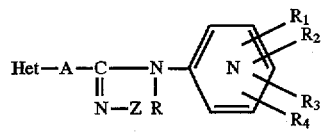 (I/c)

where

Het, A, R, $R_1$, $R_2$, $R_3$, $R_4$, Z and the ring

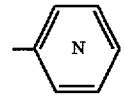

have the same definition as above,
or which derivative is reacted with a compound of formula (4):

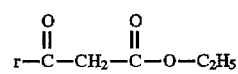 (4)

where r is an alkyl group, in order to obtain compounds of formula (5):

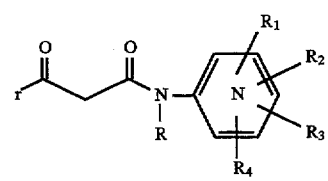 (5)

in which r, R, $R_1$, $R_2$, $R_3$, and $R_4$ are as defined above,
which compounds are reacted with a compound of formula Het—H where Het is as defined in formula (I), in order to obtain compounds of formula (I/d),

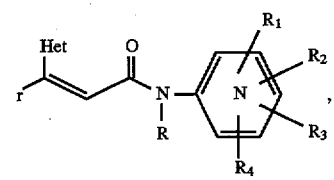 (I/d)

in which

Het, r, R, $R_1$, $R_2$, $R_3$, and $R_4$ are as defined above,
which compounds of formula (I/d) may, if so desired, be reduced by the action of sodium borohydride, for example, to give compounds of formula (I/e):

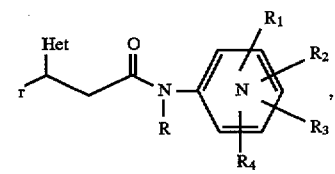 (I/e)

in which

Het, r, R, $R_1$, $R_2$, $R_3$, and $R_4$ are as defined above,
or alternatively which compounds, in the case where Het represents a pyrrolidine group, may react with alkyl chlorooximidoacetate of formula (6):

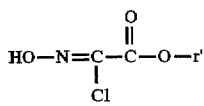

where r' is an alkyl group, to give compounds of formula (I/f):

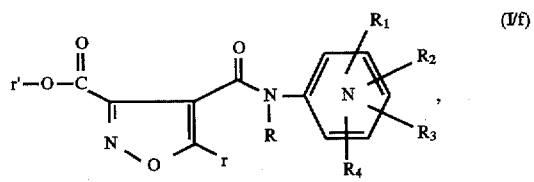

in which r, r', R, $R_1$, $R_2$, $R_3$, and $R_4$ are as defined above, which compounds of formula (I/f) may, if so desired, be reacted with lithium hydroxide, in order to obtain compounds of formula (I/g):

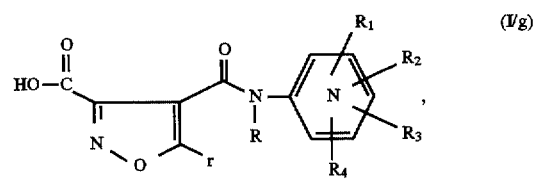

in which r, R, $R_1$, $R_2$, $R_3$, and $R_4$ are as defined above, which derivatives of formula (I/a), (I/b), (I/c), (I/d), (I/e), (I/f) and (I/g) may, if so desired, be converted into pyridine N-oxides by the action of aqueous hydrogen peroxide solution, the derivatives of formula (I/a), (I/b), (I/c), (I/d), (I/e), (I/f) and (I/g) and the N-oxides thereof forming the set of derivatives of formula (I), the enantiomers and diastereoisomers of which derivatives of formula (I) may be separated and may be salified with a pharmaceutically acceptable acid or base.

The compounds of formula (I) possess advantageous pharmacological properties.

Study of these properties has, indeed, shown that the derivatives of formula (I) were not toxic and were endowed with anti-inflammatory activity, which manifests itself both topically and systemically, as well as diuretic activity.

This spectrum of activity thus makes the compounds of the present invention useful in the treatment of chronic or acute arthritis and useful in a certain number of indications such as inflammatory rheumatism, rheumatoid polyarthritis, rheumatoid spondylitis, arthrosis, articular rheumastism and lumbago. On account of their topical activity, the compounds of the invention are useful in the treatment of certain skin disorders such as psoriasis and eczema. In addition, on account of their diuretic activity, the compounds of the invention are useful in the treatment of renal inflammatory diseases, nephritis, glomerulonephritis and pyelonephritis.

Another subject of the present invention is the pharmaceutical compositions containing a compound of formula (I), or one of the addition salts thereof with a pharmaceutically acceptable acid or base, in combination with one or more pharmacologically acceptable excipients.

Among the pharmaceutical compositions according to the invention, there may more particularly be mentioned, as examples and in a non-limiting manner, those which are suitable for oral, parenteral, nasal, rectal, perlingual, ocular, cutaneous, transcutaneous, percutaneous or pulmonary administration and especially injectable preparations, aerosols, eye drops or nasal drops, suppositories, plain, film-coated or sugar-coated tablets, gelatin capsules, wafer capsules, creams, ointments and dermal gels.

The appropriate dosage varies depending on the age, sex and weight of the patient, the route of administration, the nature of the complaint and treatments which are possibly associated therewith, and ranges between 1 mg and 5 grams per 24 hours, preferably between 1 mg and 100 mg per 24 h, more particularly between 1 and 10 mg per 24 h, for example 10 mg.

The examples which follow illustrate the invention and do not limit it in any way.

The infrared spectra are run as the potassium bromide pastille containing about 1% of the product to be analyzed.

The starting materials used are either commercially available or are accessible to those skilled in the art from the literature and from the preparations which do not form part of the invention but which are useful for preparing some products of the invention.

PREPARATION

5-BROMO-2,3-DIAMINO 4,6-DIMETHYLPYRIDINE

STAGE A

2-AMINO-5-BROMO-4,6-DIMETHYLPYRIDINE 6.1 g (50 mmol) of 2-amino-4,6-dimethylpyridine are dissolved in 50 ml of acetic acid. A solution of 8 g (50 mmol) of bromine in 50 ml of acetic acid is added dropwise using a dropping funnel. The reaction medium is allowed to return to room temperature and the stirring is continued for 3 hours. The mixture is cooled in an ice bath and 40% sodium hydroxide is then added until the pH is basic. The mixture is filtered and dried. The residue is taken up in a little isopropyl ether and then chromatographed on silica gel, eluting with this same solvent. The expected product is collected in the form of white crystals. It is recrystallized from absolute ethanol.

Yield: 69%

STAGE B

2-AMINO-5-BROMO-4,6-DIMETHYL-3-NITROPYRIDINE 4 g (20 mmol) of the product obtained in Stage A are dissolved in 16 ml of concentrated sulfuric acid with stirring and cooling in ice. The solution is brought to 55° C. and 1.3 ml of concentrated nitric acid are added dropwise, care being taken to maintain the temperature between 55° and 60° C. The stirring is continued for 20 minutes and the mixture is then poured onto crushed ice. The product is precipitated by addition of 40% sodium hydroxide. It is filtered off, washed with water and then dried. 3.7 g of product are thus collected. The product is recrystallized from 95° C. ethanol.

Yield: 75%

Melting point: 169° C.

STAGE C

5-BROMO-2,3-DIAMINO-4,6-DIMETHYLPYRIDINE

A solution of 4.1 g (21.6 mmol) of $SnCl_2$ in 20 ml of concentrated HCl is cooled in an ice bath. 1.32 g (5.4 mmol) of product obtained in Stage B are added gradually. The mixture is heated at 80° C. for 30 minutes. It is allowed to cool and then poured onto crushed ice. The resulting mixture is basified by addition of sodium hydroxide. The precipitate formed is filtered off, washed with water and then dried. 1.06 g of white powder are thus collected. The product is recrystallized from toluene.

Yield: 90%

Melting point: 183° C.

EXAMPLE 1

N-(4,6-DIMETHYL-2-PYRIDYL)-2-THIENYLACETAMIDE 9.22 g of triphenylphosphine, 6.93 ml of trichlorobromomethane, 5 g of 2-thienylacetic acid and 8.50 g of 2-amino-4,6-dimethylpyridine are dissolved in 120 ml of tetrahydrofuran. The mixture is brought to reflux and filtered, and the filtrate is concentrated; the residue is chromatographed on silica gel, eluting with dichloromethane, and the product obtained is recrystallized from isopropyl ether.

Yield: 78%

Melting point: 124°–125° C.

Elemental composition

Calculated: C 63.33H 5.68N 11.36 Found: C 63.26H 5.69N 11.34

Spectral characteristics

Infrared: 3265 cm$^{-1}$ vNH

Nuclear Magnetic Resonance (solvent CDCl$_3$)

Pyridine ring:

4-CH$_3$: 2.29 ppm singlet

6-CH$_3$: 2.36 ppm singlet

H$_3$: 7.88 ppm singlet

H$_5$: 6.72 ppm singlet $\underline{CH_2}$—CO: 3.91 ppm singlet

EXAMPLE 2

N-ETHYL-N-(4,6-DIMETHYL-2-PYRIDYL)-2-THIENYLACETAMIDE 3.4 g of 2-chloro-1-methylpyridinium iodide are dissolved in methylene chloride, followed by addition of:

1.89 g of 2-thienylacetic acid 2 g of 2-ethylamino-4,6-dimethylpyridine 4.6 ml of triethylamine The mixture is brought to reflux. When the reaction is complete, the mixture is filtered and evaporated to dryness; the residue is extracted; the organic phases are combined and dried. The solvent is evaporated off and the residue is chromatographed in a dichloromethane/ethanol mixture. An oily product is obtained.

Yield: 88%

Refractive index: 1,561

Spectral characteristics

Nuclear Magnetic Resonance (solvent CDCl$_3$) CH$_2$-CH$_3$: triplet, CH$_3$, 3H, δ1: 1.12 ppm $\underline{CH_2}$—CH$_3$: quartet, $\underline{CH_2}$, 2H, δ: 3.80 ppm

EXAMPLE 3

N-HEXYL-N-(4,6-DIMETHYL-2-PYRIDYL)-2-THIENYLACETAMIDE

The process is performed as in Example 2, but replacing the 2-ethylamino-4,6-dimethylpyridine by 2-hexylamino-4,6-dimethylpyridine. The title product is obtained.

Yield: 60%

Refractive index: 1,547

Spectral characteristics $^1$H Nuclear Magnetic Resonance (solvent CDCl$_3$)

CH$_3$—CH$_2$: triplet 3H:0.83 ppm CH$_3$—CH$_2$—$\underline{CH_2}$—CH$_2$—CH$_2$—CH$_2$—N: multiplet 6H: 1.26 ppm $\overline{CH_3—CH_2—CH_2}$—CH$_2$—CH$_2$—CH$_2$—N: multiplet 2H: 1.51 ppm $\underline{CH_2}$—N: triplet 2H: 3.78 ppm.

EXAMPLE 4

N-(5-BROMO-4,6-DIMETHYL-2-PYRIDYL)-2-THIENYLACETAMIDE

By performing the process as in Example 2, but replacing the 2-ethylamino-4,6-dimethylpyridine by 2-amino-5-bromo-4,6-dimethylpyridine obtained in Stage A of the preparation, the title product is obtained.

Recrystallization solvent: acetone

Yield: 86%

Melting point: 192° C.

Spectral characteristics $^1$H Nuclear Magnetic Resonance (solvent CDCl$_3$) CH$_2$: singlet, 2H: 3.94 ppm

EXAMPLE 5

N-(3,5-DIBROMO-4,6-DIMETHYL-2-PYRIDYL)-2-THIENYLACETAMIDE

By performing the process as in Example 2, but replacing the 2-ethylamino-4,6-dimethylpyridine by 2-amino-3,5-dibromo-4,6-dimethylpyridine, the title product is obtained.

Melting point: 154° C.

EXAMPLE 6

N-(3,5-DICHLORO-2-PYRIDYL)-2-THIENYLACETAMIDE

By performing the process as in Example 1, but replacing the 2-amino-4,6-dimethylpyridine by 2-amino-3,5-dichloropyridine, the title product is obtained.

Recrystallization: isopropyl ether

Yield: 33%

Melting point: 144°–145° C.

Spectral characteristics

Infrared 3240 cm$^{-1}$, vNH 1680 cm$^{-1}$, vCO $^1$H Nuclear Magnetic Resonance (solvent CDCl$_3$) CH$_2$: singlet 2H: 4.17 ppm

EXAMPLE 7

N-(2-AMINO-5-BROMO-4,6-DIMETHYL-3-PYRIDYL)-2-THIENYL ACETAMIDE

By performing the process as in Example 1, but replacing the 2-amino-4,6-dimethylpyridine by 5-bromo-2,3-diamino-4,6-dimethylpyridine (preparation), the title product is obtained.

Recrystallization solvent: acetone

Yield: 49%

Melting point: 202° C.

Spectral characteristics $^1$H Nuclear Magnetic Resonance (solvent CDCl$_3$) CH$_2$: singlet 2H; 4.01 ppm

EXAMPLE 8

N-(4,6-DIMETHYL-2-PYRIDYL)-5-BROMO-2-THIENYLACETAMIDE

By performing the process as in Example 1, but replacing the 2-thienylacetic acid by 2-(5-bromo)thienylacetic acid, the title product is obtained.

Melting point: 87° C.
Spectral characteristics
$^1$H Nuclear Magnetic Resonance (CDCl$_3$) CH$_2$: singlet 2H: 3.83 ppm

EXAMPLE 9

N-(4,6-DIMETHYL-2-PYRIDYL)-3-THIENYLACETAMIDE

By performing the process as in Example 1, but replacing the 2-thienylacetic acid by 3-thienylacetic acid, the title product is obtained.

Recrystallization: isopropyl ether
Yield: 65%
Melting point: 123°–124° C.
Spectral characteristics
Infrared 1660 cm$^{-1}$: νCO
$^1$H Nuclear Magnetic Resonance (CDCl$_3$) CH$_2$—CO singlet 2H; 3.74 ppm.

EXAMPLE 10

N-(5-BROMO-4,6-DIMETHYL-2-PYRIDYL)-3-THIENYLACETAMIDE

By performing the process as in Example 4, but replacing the 2-thienylacetic acid by 3-thienylacetic acid, the title product is obtained.

Recrystallization: acetone
Yield: 55%
Melting point: 211° C.
Spectral characteristics
Infrared 1650 cm$^{-1}$: νCO
$^1$H Nuclear Magnetic Resonance (CDCl$_3$) CH$_2$CO singlet 2H; 3.76 ppm.

EXAMPLE 11

N-(5-BROMO-2-PYRIDYL)-3-THIENYLACETAMIDE

By performing the process as in Example 9, but replacing the 2-amino 4,6-dimethylpyridine by 2-amino-5-bromopyridine, the title product is obtained.

Recrystallization solvent: isopropyl ether
Yield: 50%
Melting point: 117° C.
Spectral characteristics
Infrared 1665 cm$^{-1}$; νCO p $^1$H Nuclear Magnetic Resonance (solvent CDCl$_3$) CH$_2$: singlet 2H; 3.72 ppm

EXAMPLE 12

N-(3,5-DICHLORO-2-PYRIDYL)-3-THIENYLACETAMIDE

By performing the process as in Example 9, but replacing the 2-amino-4,6-dimethylpyridine by 2-amino-3,5-dichloropyridine, the title product is obtained.

Recrystallization: isopropyl ether
Yield: 30%
Melting point: 159°–160° C.
Spectral characteristics
Infrared 1680 cm$^{-1}$: νCO
$^1$H Nuclear Magnetic Resonance (solvent CDCl$_3$) CH$_2$: singlet; 2H; 3.97 ppm.

EXAMPLE 13

N-(3,5 DIBROMO-4,6-DIMETHYL-2-PYRIDYL)-3-THIENYLACETAMIDE

By performing the process as in Example 9, but replacing the 2-amino-4,6-dimethylpyridine by 2-amino-3,5-dibromo-4,6-dimethylpyridine, the title product is obtained.

Melting point: 157° C.

EXAMPLE 14

N-(4,6-DIMETHYL-2-PYRIDYL)-2-BROMO-3-THIENYLACETAMIDE

By performing the process as in Example 1, but replacing the 5-bromo-2-thienylacetic acid by 2-bromo-3-thienylacetic acid, the title product is obtained.

Melting point: 72° C.
Spectral characteristics
$^1$H Nuclear Magnetic Resonance (CDCl$_3$) CH$_2$: singlet; 2H; 3.70 ppm.

EXAMPLE 15

N-(4,6-DIMETHYL-2-PYRIDYL)-2,5-DIBROMO-3-THIENYLACETAMIDE

By performing the process as in Example 1, but replacing the 2-thienylacetic acid by 2,5-dibromo-3-thienylacetic acid, the title product is obtained.

Melting point: 109° C.
Spectral characteristics
$^1$H Nuclear Magnetic Resonance (CDCl$_3$) CH$_2$: singlet; 2H; 3.64 ppm

EXAMPLE 16

N-ETHYL-N-(4,6-DIMETHYL-2-PYRIDYL)-3-THIENYLACETAMIDE

By performing the process as in Example 2, but replacing the 2-thienylacetic acid by 3-thienylacetic acid, the oily title product is obtained.

Yield: 75%
Refractive index: 1,571
Spectral characteristics
Infrared 1650cm$^{-1}$ νCO
$^1$H Nuclear Magnetic Resonance (solvent CDCl$_3$) CH$_3$—CH$_2$: triplet 3H; δ: 1.12 ppm CH$_3$—CH$_2$: quartet 2H; δ: 3.33 ppm CH$_2$—CO: singlet 2H; δ: 3.55 ppm

EXAMPLE 17

N-(2-AMINO-5-BROMO-4,6-DIMETHYL-3-PYRIDYL)-3-THIENYLACETAMIDE

By performing the process as in Example 7, but replacing the 2-thienylacetic acid by 3-thienylacetic acid, the title product is obtained.

Recrystallization: acetone
Yield: 50%
Melting point: 194° C.
Spectral characteristics
Infrared 1635 cm$^{-1}$ νCO
$^1$H Nuclear Magnetic Resonance (solvent CDCl$_3$) CH$_2$: singlet 2H; 3.84 ppm.

EXAMPLE 18

N-HEXYL-N-(4,6-DIMETHYL-2-PYRIDYL)-3-THIENYLACETAMIDE

By performing the process as in Example 3, but replacing the 2-thienylacetic acid by 3-thienylacetic acid, the title product is obtained.

EXAMPLE 19

N-(4,6-DIMETHYL-2-PYRIDYL)-2-CHLORO-3-BENZO[b]THIENYLACETAMIDE

By performing the process as in Example 1, but replacing the 2-thienylacetic acid by 2-chloro-3-benzo[b]thienylacetic acid, the title product is obtained.

Recrystallization: isopropyl ether

Yield: 55%

Melting Point: 123°–124° C.

Spectral characteristics

Infrared 1660 cm$^{-1}$ vCO $^1$H Nuclear Magnetic Resonance $CH_2$: singlet; 2H; 3.91 ppm 4-$CH_3$: singlet; 3H; 2.22 ppm 6-$CH_3$: singlet; 3H; 3.30 ppm.

EXAMPLE 20

N-(4,6-DIMETHYL-2-PYRIDYL)-4-OXO[4H]BENZOPYRAN-2-YLCARBOXAMIDE

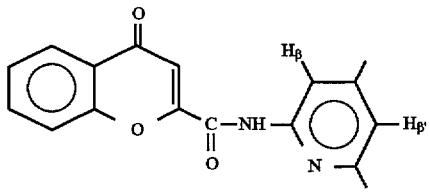

By performing the process as in Example 1, but replacing the 2-thienylacetic acid by 4-oxo[4H]benzopyran-2-ylcarboxylic acid, the title product is obtained.

Recrystallization: isopropyl ether

Yield: 60%

Melting point: 195° C.

Spectral characteristics $^1$H Nuclear Magnetic Resonance (solvent $CDCl_3$) $H_\beta'$: singlet 1H; 6.85 ppm $H_\beta$: singlet 1H; 8.02 ppm

EXAMPLE 21

N-(4,6-DIMETHYL-2-PYRIDYL)-2-PYRAZINECARBOXAMIDE 3 g of 2-pyrazinecarboxylic acid are dissolved in 20 ml of thionyl chloride. The reactants are left in contact for 30 minutes at about 60° C. The excess thionyl chloride is evaporated off and the acid chloride obtained is washed several times.

This acid chloride thus obtained is taken up in 20 ml of dichloroethane. In parallel, 3 g of 2-amino-4,6-dimethylpyridine are dissolved in 30 ml of dichloroethane. 3 ml of triethylamine are added, followed by the acid chloride solution prepared above. The reactants are left in contact for 60 minutes. The residue is filtered off and then evaporated. The product is chromatographed on a column of silica eluting with dichloromethane.

Recrystallization: isopropyl ether

Yield: 75%

Melting point: 123°–125° C.

Spectral characteristics

Infrared 1690 cm$^{-1}$: vCO $^1$H Nuclear Magnetic Resonance ($CDCl_3$) $CH_3$(4): singlet 3H; 2.37 ppm $CH_3$(6): singlet 3H; 2.46 ppm.

EXAMPLE 22

N-(5-BROMO-4,6-DIMETHYL-2-PYRIDYL)-2-PYRAZINECARBOXAMIDE

By performing the process as in Example 4, but replacing the 2-thienylacetic acid by 2-pyrazinecarboxylic acid, the title product is obtained.

Recrystallization: acetone

Yield: 60%

Melting point: 206° C.

Spectral characteristics

Infrared 1680 cm$^{-1}$: vCO $^1$H Nuclear Magnetic Resonance ($CDCl_3$) H (pyridine): singlet; 8.17 ppm $H_6$(pyrazine): resolved doublet: 1H; 8.62 ppm $H_5$(pyrazine): doublet: 1H; 8.83 ppm, J5.6; 2.40 Hz

EXAMPLE ≦

N-(3,5-DIBROMO-4,6-DIMETHYL-2-PYRIDYL)-2-PYRAZINECARBOXAMIDE

By performing the process as in Example 5, but replacing the 2-thienylacetic acid by 2-pyrazinecarboxylic acid, the title compound is obtained.

Melting point: 166° C.

EXAMPLE 24

N-(4,6-DIMETHYL-2-PYRIDYL)-2-PYRAZINETHIOCARBOXAMIDE 2.5 g of product obtained in Example 21 and 5.31 g of Lawesson's reagent are dissolved in 50 ml of toluene, and the solutions maintained at reflux for 4 h. It is filtered and the solvent is evaporated off. The product is purified by chromatography on silica gel, eluting with dichloromethane.

The product is collected and recrystallized from isopropyl ether.

Yield: 45%

Melting point: 123° C.

Spectral characteristics

Infrared 1665 cm$^{-1}$: vC=S $^1$H Nuclear Magnetic Resonance (solvent DMSO-$d_6$) $CH_3$(4): singlet 3H; 2.43 ppm $CH_3$(6): singlet 3H; 2.52 ppm

EXAMPLE 25

N-(4,6-DIMETHYL-2-PYRIDYL)-2-PYRAZINECARBOXAMIDE HYDRAZONE

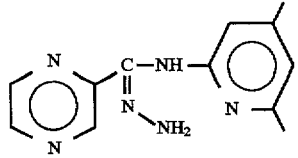

To 1 g of compound of Example 24 dissolved in 30 ml of ethanol is added 0.6 ml of hydrazine monohydrate and the mixture is left stirring for 30 minutes at room temperature. The reaction medium is then poured into ice-water. It is stirred vigorously for 20 minutes. The mixture is filtered and dried and the residue is recrystallized from isopropyl ether.

Yield: 73%

Melting point: 156° C.

Spectral characteristics

Infrared 3350 cm$^{-1}$ νNH $^1$H Nuclear Magnetic Resonance (CDCl$_3$) CH$_3$(4): singlet 3H; 2.25 ppm CH$_3$(6): singlet 3H; 2.40 ppm

N-(4,6-DIMETHYL-2-PYRIDYL)-2-PYRAZINECARBAMIDOXIME

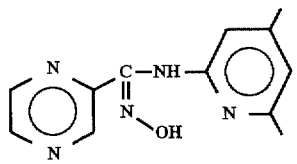

1.65 g of derivative obtained in Example 24 and 45 ml of ethanol are introduced into a round-bottomed flask. The derivative is dissolved under hot conditions, and 2.34 g of hydroxylamine hydrochloride are added, followed by 1.79 g of sodium carbonate dissolved in 20 ml of water. The mixture is maintained at reflux for 30 minutes. The reaction medium is diluted in water, filtered and dried. The product is collected and recrystallized from a methanol/chloroform mixture.

Yield: 80%

Melting point: 191° C.

Spectral characteristics

Infrared 3270 cm$^{-1}$ ν(HN) 2500–2900 cm$^{-1}$ ν(OH)

$^1$H Nuclear Magnetic Resonance $^1$H (DMSO-d$_6$) CH$_3$(4): singlet 3H; 1.80 ppm CH$_3$(6): singlet 3H; 2.17 ppm

EXAMPLE 27

N-(4,6-DIMETHYL-2-PYRIDYL)-O-METHYL-2-PYRAZINECARBAMIDOXIME

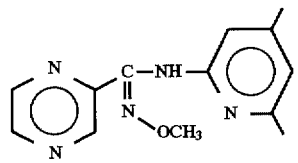

By performing the process as in Example 26 but replacing the hydroxylamine hydrochloride by methoxylamine hydrochloride, the title product is obtained.

Recrystallization: methanol

Yield: 88%

Melting point: 133° C.

Spectral characteristics

Infrared 1610–1560 cm$^{-1}$: νCN $^1$H Nuclear Magnetic Resonance (CDCl$_3$) CH$_3$(4): singlet 3H; 2.10 ppm CH$_3$(6): singlet 3H; 2.15 ppm OCH$_3$: singlet 3H; 4.02 ppm

EXAMPLE 28

N-(4,6-DIMETHYL-2-PYRIDYL)-O-BENZYL-2-PYRAZINECARBAMIDOXIME

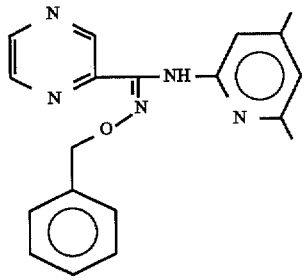

By performing the process as in Example 26, but replacing the hydroxylamine hydrochloride by benzyloxylamine hydrochloride, the title product is obtained.

Melting point: 84° C.

EXAMPLE 29

N-(4,6-DIMETHYL-2-PYRIDYL)-N'-METHYL-2-PYRAZINECARBOXAMIDINE

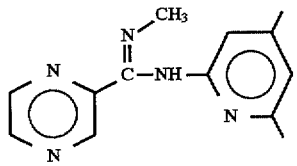

1.23 g of derivative obtained in Example 24 and 1.95 g of aqueous 40% methylamine solution are added to a round-bottomed flask containing ethanol. The mixture is left to stir at room temperature, then filtered and evaporated. The oil obtained is crystallized from diethyl ether and recrystallized from isopropyl ether.

Yield: 64%

Melting point: 103–104° C.

Spectral characteristics

Infrared 1625, 1610 cm$^{-1}$ $^1$H Nuclear Magnetic Resonance (solvent DMSO-d$_6$) CH$_3$(4): singlet 3H; 2.03 ppm CH$_3$(6): singlet 3H; 2.18 ppm N—CH$_3$: singlet 3H; 2.91 ppm

EXAMPLE 30

N-(4,6-DIMETHYL-2-PYRIDYL)-2-PYRAZINECARBOXAMIDINE

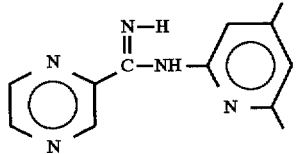

1.2 g (4.91 mmol) of product obtained in Example 24 and 40 ml of ethanol are introduced into a two-necked round-bottomed flask. A stream of ammonia gas is bubbled through. The insoluble material is filtered off and the solvent is then evaporated off. The residue is recrystallized from isopropyl ether.

Yield: 95%
Melting point: 148° C.
Spectral characteristics
  Infrared vCN 1625, 1600 cm$^{-1}$
  $^1$H Nuclear Magnetic Resonance (CDCl$_3$) CH$_3$(4) singlet 3H: 2.31 ppm CH$_3$(6) singlet 3H: 2.49 ppm

EXAMPLE 31

N-(2-AMINO-5-BROMO-4,6-DIMETHYL-3-PYRIDYL)-2-PYRAZINECARBOXAMIDE

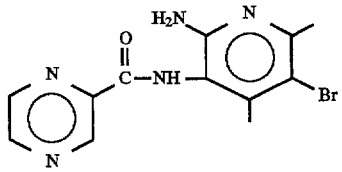

By performing the process as in Example 7, but replacing the 2-thienylacetic acid by 2-pyrazinecarboxylic acid, the title product is obtained.
Yield: 52%
Melting point: 224° C.
Spectral characteristics
  $^1$H Nuclear Magnetic Resonance (CDCl$_3$) CH$_3$(4): singlet (3H); 2.35 ppm CH$_3$(6): singlet (3H); 2.56 ppm

EXAMPLE 32

N-(4,6-DIMETHYL-2-PYRIDYL)-2-PYRAZINECARBOXAMIDE N-OXIDE

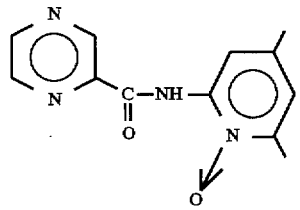

A solution of 10 ml of glacial acetic acid and 0.7 ml of aqueous hydrogen peroxide solution (35%) are added, with stirring, to 1 g of compound obtained in Example 21. The reaction medium is heated at 70° C. for 7 h and then concentrated under reduced pressure and at low temperature.

The residual solution is cooled. The white solid obtained is filtered off. It is washed with ice-water, dried and purified by chromatography on silica gel. The residue is recrystallized from a methylene chloride/isopropyl ether mixture.

Yield: 66%
Melting point: 210° C.
Spectral characteristics
  Infrared 1225 cm$^{-1}$: vNO
  $^1$H Nuclear Magnetic Resonance (CDCl$_3$) H$_6$: resolved doublet, 1H, H$_6$

EXAMPLE 33

N-(4,6-DIMETHYL-2-PYRIDYL)-2-THIENYLACETAMIDE N-OXIDE

By performing the process as in Example 32, but replacing the N-(4,6-dimethyl-2-pyridyl)-2-pyrazinecarboxamide (obtained in Example 21) by N-(4,6-dimethyl-2-pyridyl)-2-thienylacetamide (obtained in Example 1), the title product is obtained.

Melting point: 154°–155° C.

EXAMPLE 34

N-(4,6-DIMETHYL-2-PYRIDYL)-3-THIENYLACETAMIDE N-OXIDE

By performing the process as in Example 32, but using the compound obtained in Example 9, the title product is obtained.

Melting point: 154° C.

EXAMPLES 35 TO 41

By performing the process as in Examples 24 to 30 but starting with N-(4,6-dimethyl-2-pyridyl)-2-thienylacetamide, the following are respectively obtained.

EXAMPLE 35

N-(4,6-DIMETHYL-2-PYRIDYL)-2-THIENYLTHIOACETAMIDE

Melting point: 64° C.

EXAMPLE 36

N-(4,6-DIMETHYL-2-PYRIDYL)-2-THIENYLACETAMIDE HYDRAZONE

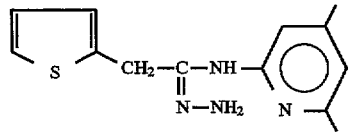

EXAMPLE 37

N-(4,6-DIMETHYL-2-PYRIDYL)-2-THIENYLACETAMIDOXIME

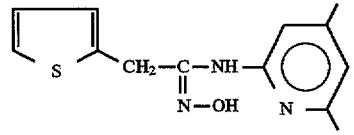

EXAMPLE 38

N-(4,6-DIMETHYL-2-PYRIDYL)-O-METHYL-2-THIENYLACETAMIDOXIME

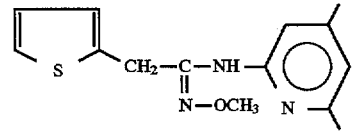

EXAMPLE 39

N-(4,6-DIMETHYL-2-PYRIDYL)-O-BENZYL-2-THIENYLACETAMIDOXIME

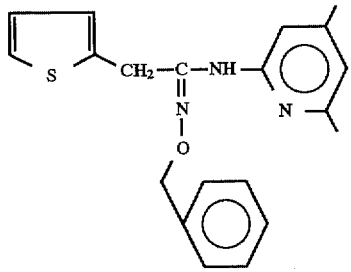

Melting point: 87° C.

EXAMPLE 40

N-(4,6-DIMETHYL-2-PYRIDYL)-N'-METHYL-2-THIENYLACETAMIDINE

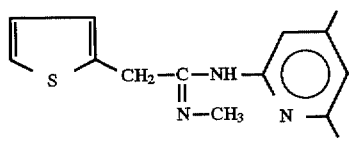

EXAMPLE 41

N-(4,6-DIMETHYL-2-PYRIDYL)-2-THIENYLACETAMIDINE

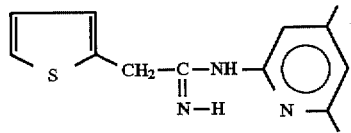

EXAMPLE 42 TO 48

By performing the process as in Examples 24 to 30 but starting with N-(4,6-dimethyl-2-pyridyl)-3-thienylacetamide, the following are respectively obtained:

EXAMPLE 42

N-(4,6-DIMETHYL-2-PYRIDYL)-3-THIENYLTHIOACETAMIDE

Melting point: 69° C.

EXAMPLE 43

N-(4,6-DIMETHYL-2-PYRIDYL)-3-THIENYLACETAMIDE HYDRAZONE

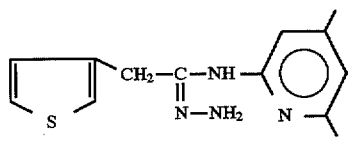

EXAMPLE 44

N-(4,6-DIMETHYL-2-PYRIDYL)-3-THIENYLACETAMIDOXIME

Melting point: 131° C.

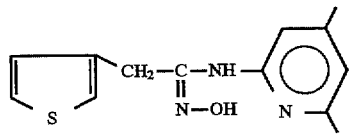

EXAMPLE 45

N-(4,6-DIMETHYL-2-PYRIDYL)-3-THIENYL-O-METHYLACETAMIDOXIME

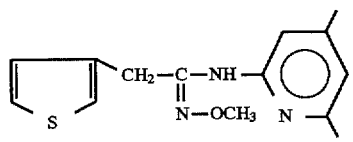

EXAMPLE 46

N-(4,6-DIMETHYL-2-PYRIDYL)-3-THIENYL-O-BENZYLACETAMIDOXIME

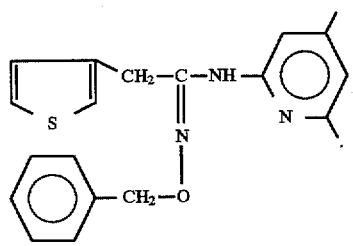

EXAMPLE 47

N-(4,6-DIMETHYL-2-PYRIDYL)-N'-METHYL-3-THIENYLACETAMIDINE

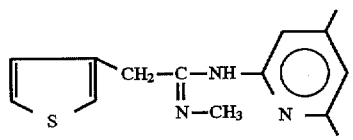

EXAMPLE 48

N-(4,6-DIMETHYL-2-PYRIDYL)-3-THIENYLACETAMIDINE

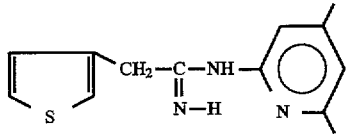

EXAMPLE 49

N-(4,6-DIMETHYL-5-NITRO-2-PYRIDYL)-2-PYRAZINECARBOXAMIDE

By performing the process as in Example 22 but starting with 2-amino-5-nitro-4,6-dimethylpyridine, the title product is obtained.

Melting point: 158° C.

EXAMPLE 50

N-(4,6-DIMETHYL-2-PYRIDYL)-PHTHALIMIDOACETAMIDE

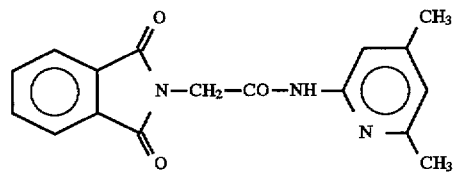

By performing the process as in Example 1 but replacing the 2-thienylacetic acid by 2-phthalimidoacetic acid, the title product is obtained.

Melting point: 212°–213° C.
Spectral characteristics $^1$H Nuclear Magnetic Resonance (solvent CDCl$_3$) CH$_2$: singlet; 2H: 4,54 ppm

EXAMPLE 51

N-(4,6-DIMETHYL-2-PYRIDYL)-4-PYRIDINECARBOXAMIDE

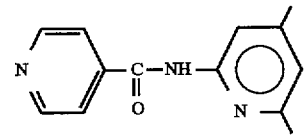

By performing the process as in Example 1 but replacing the 2-thienylacetic acid by 4-pyridinecarboxylic acid, the title product is obtained.

Melting point: 142° C.

EXAMPLE 52

N-(4,6-DIMETHYL-2-PYRIDYL)-(2-METHYLTHIO-3-PYRIDYL)ACETAMIDE

By performing the process as in Example 1 but replacing the 2-thienylacetic acid by 2-methylthio-3-pyridinecarboxylic acid, the title product is obtained.

Melting point: 164° C.

EXAMPLE 53

N-(4,6-DIMETHYL-2-PYRIDYL)-(2-HYDROXY-3-PYRIDYL)CARBOXAMIDE

By performing the process as in Example 1 but replacing the 2-thienylacetic acid by 2-hydroxy-3-pyridinecarboxylic acid, the title product is obtained.

Melting point: 245° C.

EXAMPLE 54

N-(4,6-DIMETHYL-2-PYRIDYL)-(2—CHLORO-3-PYRIDYL)CARBOXAMIDE

By performing the process as in Example 1 but replacing the 2-thienylacetic acid by 2-chloro-3-pyridinecarboxylic acid, the title product is obtained.

Melting point: 91° C.

EXAMPLE 55

N-(4,6-DIMETHYL-2-PYRIDYL)-2-CHLOROBENZO[b]THIENYL-3-CARBOXAMIDE

By performing the process as in Example 1 but replacing the 2-thienylacetic acid by 2-chlorobenzo[b]thienyl-3-carboxylic acid, the title product is obtained.

EXAMPLES 56 to 62

By performing the process as in Examples 24 to 30 but starting with N-(4,6-dimethyl-2-pyridyl)-2-chlorobenzo[b]thienyl-3-acetamide (compound of Example 19), the following are respectively obtained:

EXAMPLE 56

N-(4,6-DIMETHYL-2-PYRIDYL)-2-CHLOROBENZO[b]THIENYL-3-THIOACETAMIDE

EXAMPLE 57

N-(4,6-DIMETHYL-2-PYRIDYL)-2-CHLOROBENZO[b]THIENYL-3-ACETAMIDE HYDRAZONE

EXAMPLE 58

N-(4,6-DIMETHYL-2-PYRIDYL)-2-CHLOROBENZO[b]THIENYL-3-ACETAMIDOXIME

EXAMPLE 59

N-(4,6-DIMETHYL-2-PYRIDYL)-O-METHYL-2-CHLOROBENZO[b]-THIENYL-3-ACETAMIDOXIME

EXAMPLE 60

N-(4,6-DIMETHYL-2-PYRIDYL)-O-BENZYL-2-CHLOROBENZO[b]-THIENYL-3-ACETAMIDOXIME

EXAMPLE 61

N-(4,6-DIMETHYL-2-PYRIDYL)-N'-METHYL-2-CHLOROBENZO[b]-THIENYL-3-ACETAMIDINE

EXAMPLE 62

N-(4,6-DIMETHYL-2-PYRIDYL)-2-CHLOROBENZO[b]THIENYL-3-ACETAMIDINE

EXAMPLE 63

N-(4,6-DIMETHYL-2-PYRIDYL)-4-OXO[4H]BENZOPYRAN -2-YLACETAMIDE

By performing the process as in Example 1 but replacing the 2-(thien-2-yl)acetic acid by 4-oxo[4H]benzopyran-2-ylacetic acid, the title product is obtained.

EXAMPLE 64 TO 70

By performing the process as in Examples 24 to 30 but starting with N-(4,6-dimethyl-2-pyridyl)-4-oxo[4H]benzopyran-2-ylcarboxamide (compound of Example 20), the following are respectively obtained:

EXAMPLE 64
N-(4,6-DIMETHYL-2-PYRIDYL)-4-OXO[4H]
BENZOPYRAN-2-YLTHIOCARBOXAMIDE

EXAMPLE 65
N-(4,6-DIMETHYL-2-PYRIDYL)-4-OXO[4H]
BENZOPYRAN-2-YLCARBOXAMIDE
HYDRAZONE

EXAMPLE 66
N-(4,6-DIMETHYL-2-PYRIDYL)-4-OXO[4H]
BENZOPYRAN-2-YLCARBAMIDOXIME

EXAMPLE 67
N-(4,6-DIMETHYL-2-PYRIDYL)-O-METHYL-4-
OXO[4H]BENZOPYRAN-2-
YLCARBAMIDOXIME

EXAMPLE 68
N-(4,6-DIMETHYL-2-PYRIDYL)-O-BENZYL-4-
OXO[4H]BENZOPYRAN-2-
YLCARBAMIDOXIME

EXAMPLE 69
N-(4,6-DIMETHYL-2-PYRIDYL-N'-METHYL-4-
OXO[4H]BENZOPYRAN-2-
YLCARBOXAMIDINE

EXAMPLE 70
N-(4,6-DIMETHYL-2-PYRIDYL)-4-OXO[4H]
BENZOPYRAN-2-YLCARBOXAMIDINE

EXAMPLE 71 TO 77

By performing the process as in Examples 24 to 30 but starting with N-(4,6-dimethyl-2-pyridyl)-4-pyridinecarboxamide (compound of Example 51), the following are respectively obtained:

EXAMPLE 71
N-(4,6-DIMETHYL-2-PYRIDYL)-4-
PYRIDINETHIOCARBOXAMIDE

EXAMPLE 72
N-(4,6-DIMETHYL-2-PYRIDYL)-4-
PYRIDINECARBOXAMIDE HYDRAZONE

EXAMPLE 73
N-(4,6-DIMETHYL-2-PYRIDYL)-4-
PYRIDINECARBAMIDOXIME

EXAMPLE 74
N-(4,6-DIMETHYL-2-PYRIDYL)-4-PYRIDYL-O-
METHYLCARBAMIDOXIME

EXAMPLE 75
N-(4,6-DIMETHYL-2-PYRIDYL)-4-PYRIDYL-O-
BENZYLCARBAMIDOXIME

EXAMPLE 76
N-(4,6-DIMETHYL-2-PYRIDYL)-N'-METHYL-4-
PYRIDYLCARBOXAMIDINE

EXAMPLE 77
N-(4,6-DIMETHYL-2-PYRIDYL)-4-
PYRIDYLCARBOXAMIDINE

EXAMPLE 78
N-(4,6-DIMETHYL-2-PYRIDYL)-4-
PYRIDYLACETAMIDE

By performing the process as in Example 1 but replacing the 2-thienylacetic acid by 4-pyridineacetic acid, the title product is obtained.

EXAMPLE 79
N-(4,6-DIMETHYL-2-PYRIDYL)-3-
THIENYLPROPIONAMIDE

By performing the process as in Example 1 but starting with 3-thienylpropionic acid, the title product is obtained.

EXAMPLE 80
N-(4,6-DIMETHYL-2-PYRIDYL)-3-
THIENYLBUTANAMIDE

By performing the process as in Example 1 but starting with 3-thienylbutanoic acid, the title product is obtained.

EXAMPLE 81
N-(4,6-DIMETHYL-2-PYRIDYL)-3-
THIENYLPROPENAMIDE

By performing the process as in Example 1 but starting with 3-thienylpropenoic aicd, the title product is obtained.

EXAMPLE 82
N-(4,6-DIMETHYL-2-PYRIDYL)BENZOPYRAN-
3-YLCARBOXAMIDE

By performing the process as in Example 1 but starting with benzopyran-3-ylcarboxylic acid, the title product is obtained.

EXAMPLE 83
N-(4,6-DIMETHYL-2-PYRIDYL)BENZOPYRAN-
3-YLACETAMIDE

By performing the process as in Example 1, but starting with benzopyran-3-ylacetic acid, the title product is obtained.

EXAMPLE 84
N-(4,6-DIMETHYL-2-PYRIDYL)-3-
CHROMANYLCARBOXAMIDE

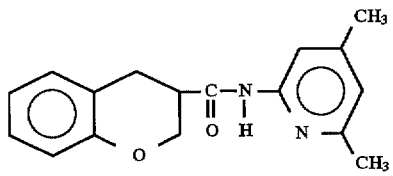

By performing the process as in Example 1 but starting with chroman-3-ylcarboxylic acid, the title product is obtained.

EXAMPLE 85
N-(4,6-DIMETHYL-2-PYRIDYL)-3-
CHROMANYLACETAMIDE

By performing the process as in Example 1 but starting with chroman-3-ylacetic acid, the title product is obtained.

EXAMPLE 86
N-(4,6-DIMETHYL-2-PYRIDYL)-5-METHYL-2-
PYRAZINECARBOXAMIDE

By performing the process as in Example 2 but replacing the 2-thienylacetic acid by 5-methyl-2-pyrazinecarboxylic acid and the 2-ethylamino-4,6-dimethylpyridine by 2-amino-4,6-dimethylpyridine, the title product is obtained in the form of a white powder which is recrystallized from an ethyl acetate/chloroform mixture (7/3).

Melting point: 169° C.

EXAMPLES 87 TO 93

By performing the process as in Examples 24 to 30 but starting with N-(4,6-dimethyl-2-pyridyl)-5-methyl-2-pyrazinecarboxamide (compound of Example 86), the following are respectively obtained:

EXAMPLE 87

N-(4,6-DIMETHYL-2-PYRIDYL)-5-METHYL-2-PYRAZINETHIOCARBOXAMIDE

Recrystallization: isopropyl ether/petroleum ether 9/1

Yield: 43%

Melting point: 129° C.

Spectral characteristics

Infrared 3260 cm$^{-1}$: vNH $^1$H Nuclear Magnetic Resonance (CDCl$_3$) CH$_3$(position 5 of the pyrazine): singlet, 3H, 2.67 ppm

EXAMPLE 88

N-(4,6-DIMETHYL-2-PYRIDYL)-5-METHYL-2-PYRAZINECARBOXAMIDE HYDRAZONE

EXAMPLE 89

N-(4,6-DIMETHYL-2-PYRIDYL)-5-METHYL-2-PYRAZINECARBOXAMIDOXIME

Melting point: 173° C.

EXAMPLE 90

N-(4,6-DIMETHYL-2-PYRIDYL)-5-METHYL-2-PYRAZINYL-O-METHYLCARBOXAMIDOXIME

Melting point: 137° C.

EXAMPLE 91

N-(4,6-DIMETHYL-2-PYRIDYL)-5-METHYL-2-PYRAZINYL-O-BENZYLCARBOXAMIDOXIME

EXAMPLE 92

N-(4,6-DIMETHYL-2-PYRIDYL)-N'-METHYL-5-METHYL-2-PYRAZINCARBOXAMIDINE

EXAMPLE 93

N-(4,6-DIMETHYL-2-PYRIDYL)-5-METHYL-2-PYRAZINECARBOXAMIDINE

EXAMPLE 94

N-(4,6-DIMETHYL-2-PYRIDYL)-3-(1-PYRROLIDINYL)-2-BUTENAMIDE

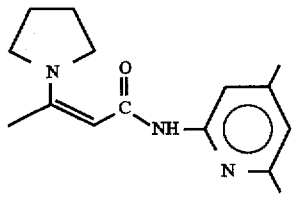

4.52 g (23.6 mmol) of N-(4,6-dimethyl-2-pyridyl)-2-acetoacetamide, obtained by condensation of a pyridine and ethyl acetoacetate, 2.02 g (28.6 mmol) of pyrrolidine and 55 ml of benzene are introduced into a 250 ml round-bottomed flask on which is fitted a Dean-Stark apparatus. The mixture is heated at reflux for one hour. The solvent is evaporated off. The crystals are washed with isopropyl ether. The title product, of ecru color, is collected.

Melting point: 132° C.

EXAMPLE 95

N-(4,6-DIMETHYL-2-PYRIDYL)-3-(1-PYRROLIDINYL)BUTANAMIDE

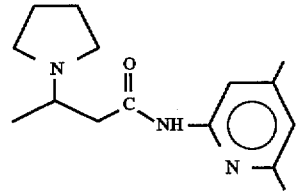

1.37 g (5.3 mmol) of the compound obtained in Example 94 and 60 ml of methanol are introduced into a 250 ml round-bottomed flask. 1 g (27 mmol) of sodium borohydride is added slowly thereto. The mixture is left stirring at room temperature for 1 h30. The solvent is evaporated off and the residue is taken up in water. This mixture is extracted with dichloromethane. The organic extracts are evaporated and the crude product is purified by passage through a column of silica gel, eluting with a dichloromethane/ethanol mixture (90/10). The product obtained is viscous and crystallizes slowly.

EXAMPLE 96

N-(4,6-DIMETHYL-2-PYRIDYL)-(3-ETHOXYCARBONYL-5-METHYL-4-ISOXAZOLYL)CARBOXAMIDE

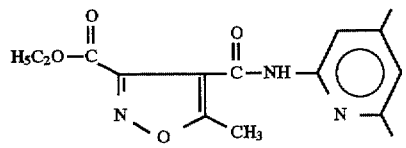

A solution of 3.5 g (13.51 mmol) of the compound obtained in Example 94 in 30 ml of dichloromethane is cooled to 0° C. 2.62 g of ethyl chlorooximidoacetate are added thereto in a single portion. The stirring is continued at 0° C. for 3 hours. The reaction medium is poured into water and the mixture is extracted with dichloromethane. The organic phase is washed with 5% hydrochloric acid solution and then with saturated sodium bicarbonate solution. The solution is dried and the solvent is evaporated off. The product is purified by passing through a column of silica gel, eluting with isopropyl ether. The product obtained is in the form of white crystals.

Melting point: 108° C.

Spectral characteristics $^1$H Nuclear Magnetic Resonance (CDCl$_3$): CH$_2$: doublet 2H: 4.60 ppm

EXAMPLE 97

N-(4,6-DIMETHYL-2-PYRIDYL)-(3-CARBOXY-5-METHYL-4-ISOXAZOLYL)CARBOXAMIDE

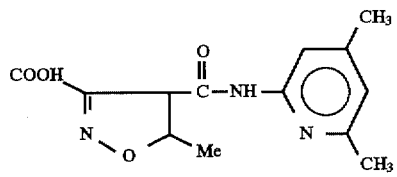

A solution of 0.27 g (11.5 mmol) of lithium hydroxide in 3 ml of water and 15 ml of methanol is cooled to −15° C. 1.5 g (5.19 mmol) of the product obtained in Example 96 are added slowly thereto with stirring. The stirring is continued for one hour. The mixture is acidified with dilute hydrochloric acid solution. The temperature is allowed to rise to 0° C. and stirring is continued for 30 min. The mixture is filtered and the title product is collected in the form of a white powder which is washed with t-butyl methyl ether.

Melting point: 183° C.

EXAMPLE 98

N-(4,6-DIMETHYL-2-PYRIDYL)-3-PIPERIDYL-2-BUTENAMIDE

By performing the process as in Example 94 but replacing the pyrrolidine by piperidine, the title product is obtained.

EXAMPLE 99

N-(4,6-DIMETHYL-2-PYRIDYL)-3-PYRROLIN-1-YL-2-BUTENAMIDE

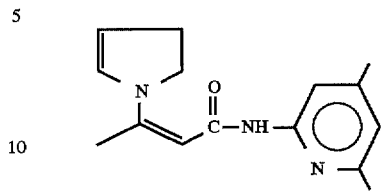

By performing the process as in Example 94 but replacing the pyrrolidine by pyrroline, the title product is obtained.

EXAMPLE 100

N-(4,6-DIMETHYL-2-PYRIDYL)-(1-METHYL-2-PYRROLYL)ACETAMIDE

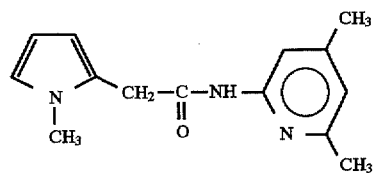

By performing the process as in Example 1 but replacing the 2-thienylacetic acid by 1-methyl-2-pyrrolylacetic acid, the title product is obtained.

Melting point: 85° C.

PHARMACOLOGICAL STUDY OF THE DERIVATIVES OF THE INVENTION

EXAMPLE A

STUDY OF THE ACUTE TOXICITY

The acute toxicity was evaluated after oral administration to batches of 8 mice (26±2 grams) of a dose of 650 mg.kg$^{-1}$. The animals were observed at regular intervals throughout the first day and daily during the 2 weeks following the treatment.

The compounds of the invention appear to be totally nontoxic. No death is observed after administration of a dose of 650 mg.kg$^{-1}$. No disorders are observed after administration of this dose.

EXAMPLE B

STUDY OF THE ANTI-INFLAMMATORY ACTIVITY

The method used is that of plantar edema using carrageenan. The procedure used is as follows: 1% carrageenan in 0.2 ml of 9% saline solution is administered into the sole of the right foot of Sprague-Dawley rats weighing 250 g on average. The volume of the paw is measured by plethysmography after one hour and after two hours.

The compounds of the invention are administered in a 10 mg/kg oral dose 30 minutes before the administration of carrageenan. A saline solution is injected into the sole of the left foot, which serves as a control.

The compounds of the invention make it possible to reduce the increase in volume of the right foot relative to that of the left foot (Table 1).

TABLE 1

| Compounds | Percentage of inhibition | |
|---|---|---|
| | 1 h | 2 h |
| 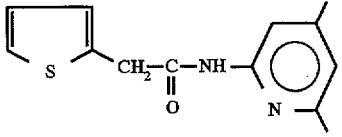<br>Example 1 | 63% | 70% |
| 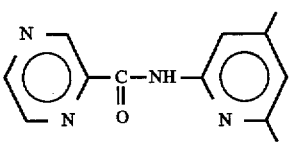<br>Example 21 | 55% | 64% |
| Indomethacin (10 mg/kg) | 24% | 64% |

The compounds of the invention very strongly inhibit the inflammation induced by carrageenan from 1 h and are more active than indomethacin, which is taken as a reference and administered under the same conditions.

EXAMPLE C
STUDY OF THE DIURETIC ACTIVITY

Groups of 3 fasted rats are used. Each group receives 25 ml/kg orally (p.o.) of distilled water administered with the products of the invention at a dose of 3 mg/kg.

The urinary volume is measured during the 6 hours following the administration.

Thus, for example, the compound of Example 25 allows the urinary volume to be increased by a factor 2.8 relative to an untreated rat.

When administered at a dose of 5 mg/kg p.o., furosemide, taken as a reference, allows the urinary volume to be increased by a factor of 3.

The diuretic power of the products of the invention is thus comparable to that of furosemide.

EXAMPLE D
DEMONSTRATION OF THE ACTIVITY AGAINST ACUTE CUTANEOUS INFLAMMATION (TOPICAL)

Phorbol ester (phorbol 12-myristate 13-acetate) (5 µg) is applied topically to the front and back surfaces of the right ear of the mouse 30 minutes after application of the vehicle (95% ethanol) or of the agent (1 mg). The difference in thickness between the right ear and the left ear (edema) is measured 6 hours after application.

The percentage of inhibition of cutaneous inflammation relative to a group of animals treated topically with 95% ethanol is calculated. The compound of Example 1, at a rate of 1 mg/ear, allows a 63% reduction of the inflammation. Indomethacin, taken as a reference, at a dose of 2.5 mg/ear, allows a 67% reduction of inflammation.

EXAMPLE E
CURATIVE ACTIVITY AND ACTIVITY AFTER REPEATED TOPICAL APPLICATION IN THE ESTABLISHED MODEL OF CHRONIC INFLAMMATION OF THE EAR SUBJECTED TO A REPEATED APPLICATION OF PHORBOL ESTER (PMA) FOR 15 DAYS ("PERTINENT" MODEL OF PSORIASIS)

Phorbol ester (1 µg) is applied topically to the front and back surfaces of the right ear of the mouse on days 0, 2, 4, 7, 9, 11 and 14. The vehicle or the agent is applied topically twice daily, on days 7, 8, 9, 10, 11, 12, 13 and 14, and once on the 15th day. On days 7, 9, 11 and 14 the vehicle or the agent is applied 30 minutes before and after the phorbol ester.

Two parameters are measured
1. Difference in thickness between the right and left ears every day and on days 0, 2, 4, 7, 9, 11 and 14, 6 hours after repeated application of the phorbol ester.

After repeated application of phorbol ester and after 15 days, the thickness reflects not only the presence of an edema and of an infiltration of lymphocyte and monocytemacrophage neutrophil type cells in the skin tissue (inflammation) but also of an increase in the thickness of the epidermis (epidermal hyperplasia secondary to a proliferation of keratinocytes). These two processes constitute the physiopathological bases of psoriasis.

2. Difference in weight ("ear punches") between the right and left ears on the 10th day. In this chronic model, 15 days after repeated application of phorbol ester, the standard anti-inflammatory agents inhibiting cyclooxygenase (indomethacin and piroxicam) are topically inactive but, however, medicinal products currently used in the treatment of psoriasis (cyclosporin A and corticoids) are topically active.

Thus, cyclosporin A and hydrocortisone were used as reference substances. A group receiving ethanol serves as a control.

The products of the invention, in topical, curative and repeated use, inhibit, between the 8th and 10th days, the chronic inflammation of the right ear (measured, on the one hand, by the difference in thickness between the right ear and the left ear, and, on the other hand, by the difference in weight between the two ears after sacrificing the animal on the 15th day) induced by a repeated application of phorbol ester in mice.

For example, at a dose of 0.5 mg/ear, the compound of Example 17 allows a 60% reduction of the difference in thickness between the two ears and allows a 38% reduction of the weight difference.

EXAMPLE F
STUDY OF AN ACTIVITY OF ANTI-ARTHRITIC TYPE IN RATS

Groups of 5 male or female Lewis rats weighing from 130 to 150 g are used. A suspension of 0.3 mg of killed Mycobacterium tuberculosis in 0.1 $cm^3$ of mineral oil (complete Freund adjuvant, CFA) is administered into the subplantar region of the right hind foot on day 1. The volumes of the hind feet are measured by water displacement on days 0, 1, 5, 14 and 18. The rats are weighed on days 0 and 18. The test products are suspended in carboxymethylcellulose and administered orally for 5 consecutive days, on days 1 to 5. In parallel, a control group is used in order to eliminate artefacts resulting from the handling of the animals. A group treated with a reference product (hydrocortisone) allows the test to be validated.

On day 18, the compound of Example 1 thus allows a 47% reduction in the volume of the right hind foot.

The products of the invention possess a powerful inhibitory action in this model, which places them as very interesting candidates for the treatment of arthritis.

PHARMACEUTICAL COMPOSITIONS

EXAMPLE A

TABLETS FOR THE TREATMENT OF INFLAMMATORY DISEASES AND RENAL DISEASES

Compounds containing a 10 mg dose of N-(4,6-dimethyl-2-pyridyl)-3-thienylacetamide

| Preparation formula for 1000 tablets | |
|---|---|
| N-(4,6-Dimethyl-2-pryidyl)-3-thienylacetamide | 10 g |
| Wheat starch | 35 g |
| Corn starch | 65 g |
| Lactose | 65 g |
| Magnesium stearate | 2 g |
| Silica | 1 g |
| Hydroxypropylcellulose | 2 g |

EXAMPLE B

OINTMENT INTENDED FOR THE TREATMENT OF PSORIASIS AND CONTAINING A 1% DOSE OF N-4,6-DIMETHYL-2-PYRIDYL)-2-THIENYLACETAMIDE

Preparation formula for 100 kg N-(4,6-Dimethyl-2-pyridyl)-2-thienylacetamide 1000 g Excipient in sufficient quantity for 100 kg (Cetyl alcohol, stearyl alcohol, isopropyl alcohol; lanolin, polyethylene glycol monostearate, distilled common laurel cherry water).

We claim:

1. A compound selected from those of formula (I):

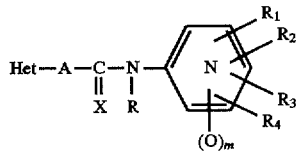

in which m is equal to 0 or 1, the symbol

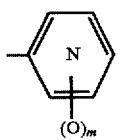

representing the pyridine ring when m is equal to 0 and pyridine N-oxide when m is equal to 1, the pyridine system

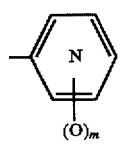

being connected to the group

which bears it either in the 2-position or in the 3-position of the pyridine;

$R_1$ and $R_2$, which may be identical or different, are chosen, independently of each other, from hydrogen, amino, alkylamino, dialkylamino, alkyl, hydroxy, alkoxy, nitro, and halogen, $R_3$ and $R_4$, which may be identical or different, are chosen, independently of each other, from amino, alkylamino, dialkylamino, alkyl, hydroxy, alkoxy, nitro, and halogen, R represents hydrogen or alkyl, A represents alkylene which is unsubstituted or substituted with one or more alkyl, or alkenylene which is unsubstituted or substituted with one or more alkyls; and Het represents a group chosen from thiophene, substituted thiophene, benzothiophene and substituted benzothiophene, X represents oxygen, sulfur, imino or imino substituted with a group chosen from alkyl, alkoxy, hydroxy, amino, arylalkyloxy and aryloxy, an enantiomer and a diastereoisomer thereof and an addition salt thereof with a pharmaceutically-acceptable acid or base, it being understood that, except where otherwise mentioned:

the term "substituted" relating to the thiophene and benzothiophene systems means that these systems are substituted with one or more groups chosen from alkyl, alkoxy, trifluoromethyl, hydroxy, halogen, thiol and alkylthio, the terms "alkyl", "alkoxy" and "alkylene", denote linear or branched groups containing 1 to 6 carbon atoms, inclusive, the term "aryl" denotes phenyl or naphthyl, and the term "alkenylene" denotes a linear or branched unsaturated chain containing 2 to 6 carbon atoms, inclusive.

2. A compound of claim 1, having the formula (IA):

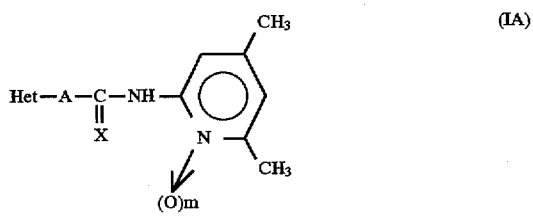

in which m represents 0 or 1, and

Het represents thiophene and A represents methylene, and

X represents oxygen, sulfur, imino or imino substitued with a hydroxyl, a methoxy, a methyl, amino or benzyloxy, an enantiomer and a diastereoisomer thereof and an addition salt thereof with a pharmaceutically-acceptable acid.

3. A compound of claim 1, which is selected from N-(4,6-dimethyl-2-pyridyl)-2-thienylacetamide, the N-oxide thereof and an addition salt thereof, with a pharmaceutically-acceptable acid.

4. A compound of claim 1, which is selected from N-(4,6-dimethyl-2-pyridyl)-3-thienylacetamide, the N-oxide thereof, and the salts thereof with a pharmaceutically-acceptable acid.

5. A pharmaceutical composition useful for treating inflammatory disorders containing as active principle at least one compound selected from those of formula (I):

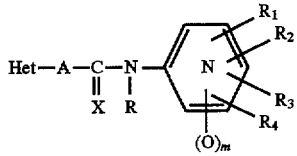

in which
m is equal to 0 or 1,
the symbol

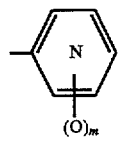

representing the pyridine ring when m is equal to 0 and pyridine N-oxide when m is equal to 1, the pyridine systems

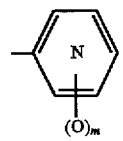

being connected to the group

which bears it either in the 2-position or in the 3-position of the pyridine ring;

$R_1$ and $R_2$, which may be identical or different, are chosen, independently of each other, from hydrogen, amino, alkylamino, dialkylamino, alkyl, hydroxy, alkoxy, nitro, and halogen, $R_3$ and $R_4$, which may be identical or different, are chosen, independently of each other, from amino, alkylamino, dialkylamino, alkyl, hydroxy, alkoxy, nitro, and halogen, R represents hydrogen or alkyl, A represents alkylene which is unsubstituted or substituted with one or more alkyl, or alkenylene which is unsubstituted or substituted with one or more alkyls; and Het represents a group chosen from thiophene, substituted thiophene, benzothiophene and substituted benzothiophene, X represents oxygen, sulfur, imino or imino substituted with a group chosen from alkyl, alkoxy, hydroxy, amino, arylalkyloxy and aryloxy, an enantiomer and a diastereoisomer thereof and an addition salt thereof with a pharmaceutically-acceptable acid or base, it being understood that, except where otherwise mentioned:

the term "substituted" relating to the thiophene and benzothiophene systems means that these systems are substituted with one or more groups chosen from alkyl, alkoxy, trifluoromethyl, hydroxy, halogen, thio and alkylthio, the terms "alkyl", "alkoxy" and "alkylene" denote linear or branched groups containing 1 to 6 carbon atoms, inclusive, the term "aryl" denotes phenyl or naphthyl, and the term "alkenylene" denotes a linear or branched unsaturated chain containing 2 to 6 carbon atoms, inclusive, in combination with one or more pharmaceutically-acceptable excipients or vehicles.

6. A pharmaceutical composition according to claim 5 wherein the compound has the formula (IA):

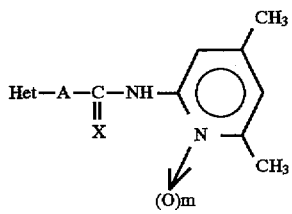

in which m represents 0 or 1, and

Het represents thiophene and A represents methylene, and X represents oxygen, sulfur, imino or imino substituted with a hydroxyl, a methoxy, a methyl, amino or benzyloxy, an enantiomer and a diastereoisomer thereof and an addition salt thereof with a pharmaceutically-acceptable acid.

7. A pharmaceutical composition according to claim 5 wherein the compound is selected from the group consisting of N-(4,6-dimethyl-2-pyridyl)-2-thienylacetamide, the N-oxide thereof, and an addition salt thereof with a pharmaceutically-acceptable acid.

8. A pharmaceutical composition according to claim 5 wherein the compound is selected from the group consisting of N-(4,6-dimethyl-2-pyridyl)-3-thienylacetamide, the N-oxide thereof, and the addition salts thereof with a pharmaceutically-acceptable acid.

9. A method of treating a mammal afflicted with an inflammatory disorder comprising the step of administering to the said mammal an amount of a compound selected from those of formula (I):

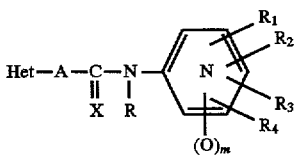

in which m is equal to 0 or 1,
the symbol

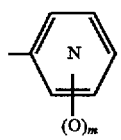

representing the pyridine ring when m is equal to 0 and pyridine N-oxide when m is equal to 1, the pyridine system

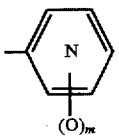

being connected to the group

which bears it either in the 2-position or in the 3-position of the pyridine ring;

$R_1$ and $R_2$, which may be identical or different, are chosen, independently of each other, from hydrogen, amino, alkylamino, dialkylamino, alkyl, hydroxy, alkoxy, nitro, and halogen, $R_3$ and $R_4$, which may be identical or different, are chosen, independently of each other, from amino, alkylamino, dialkylamino, alkyl, hydroxy, alkoxy, nitro, and halogen, R represents hydrogen or alkyl, A represents a single bond; and in this case Het represents a group chosen from benzothiophene and substituted benzothiophene, or alternatively A represents alkylene which is unsubstituted or substituted with one or more alkyl, or alkenylene which is unsubstituted or substituted with one or more alkyls; and in this case Het represents a group chosen from thiophene, substituted thiophene, benzothiophene and substituted benzothiophene, X represents oxygen, sulfur, imino or imino substituted with a group chosen from alkyl, alkoxy, hydroxy, amino, arylalkyloxy and aryloxy, an enantiomer and a diastereoisomer thereof and an addition salt thereof with a pharmaceutically-acceptable acid or base, it being understood that, except where otherwise mentioned:

the term "substituted" relating to the thiophene and benzothiophene systems means that these systems are substituted with one or more groups chosen from alkyl, alkoxy, trifluoromethyl, hydroxy, halogen, thio and alkylthio, the terms "alkyl", "alkoxy" and "alkylene" denote linear or branched groups containing 1 to 6 carbon atoms, inclusive, the term "aryl" denotes phenyl or naphthyl, the term "alkenylene" denotes a linear or branched unsaturated chain containing 2 to 6 carbon atoms, inclusive, which is effective for alleviating the said disorder.

10. A method of claim 9, wherein the compound has the formula (IA):

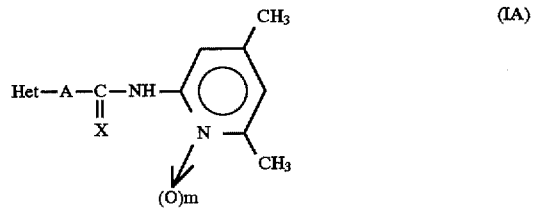

in which m represents 0 or 1, and

Het represents thiophene and A represents methylene, and

X represents oxygen, sulfur, imino or imino substituted with a hydroxyl, a methoxy, a methyl, amino or benzyloxy, an enantiomer and a diastereoisomer thereof and an addition salt thereof with a pharmaceutically-acceptable acid.

11. A method of claim 9, wherein the compound is selected from the group consisting of N-(4,6-dimethyl-2-pyridyl)-2-thienylacetamide, the N-oxide thereof, and an addition salt thereof with a pharmaceutically-acceptable acid.

12. A method of claim 9, wherein the compound is selected from the group consisting of N-(4,6-dimethyl-2-pyridyl)-3-thienylacetamide, the N-oxide thereof, and the addition salts thereof with a pharmaceutically-acceptable acid.

* * * * *

UNITED STATES PATENT AND TRADEMARK OFFICE
CERTIFICATE OF CORRECTION

PATENT NO. : 5,712,294
DATED : Jan. 27, 1998
INVENTOR(S) : J.M. Robert, O. Rideau, S. Robert-Plessard, J. Courant, G. Le Raut, D.H. Caignard, P. Renard, G. Adams It is certified that error appears in the above-indentified patent and that said Letters Patent is hereby corrected as shown below:

Column 5, line 62: "NH-Z" should read -- $NH_2$-Z --.

Column 11, line 50: Delete the "p" after "vCO".

Column 14. line 18: "$\leq$" after "EXAMPLE" should read -- 23 --.

Column 15, line 5: Insert -- EXAMPLE 26 -- on this line.

Column 31, line 67: Insert -- ring -- between "pyridine" and the ";".

Signed and Sealed this

Fourteenth Day of April, 1998

Attest:

BRUCE LEHMAN

*Attesting Officer*　　　*Commissioner of Patents and Trademarks*